(12) United States Patent
Wysor et al.

(10) Patent No.: US 6,183,414 B1
(45) Date of Patent: Feb. 6, 2001

(54) TECHNIQUE FOR RESTORING PLASTICITY TO TISSUES OF A MALE OR FEMALE ORGAN

(76) Inventors: Michael S. Wysor; Wanda D. Wysor, both of 1171 First St., Gray, TN (US) 37615

(*) Notice: Under 35 U.S.C. 154(b), the term of this patent shall be extended for 0 days.

(21) Appl. No.: 09/299,284

(22) Filed: Apr. 26, 1999

(51) Int. Cl.⁷ ........................................................ A61F 5/00
(52) U.S. Cl. .................................................................. 600/38
(58) Field of Search ............................. 600/38, 39, 41

(56) References Cited

U.S. PATENT DOCUMENTS

| | | | | |
|---|---|---|---|---|
| 1,225,341 | * | 3/1917 | Lederer | 600/38 |
| 4,378,008 | * | 3/1983 | Osbon et al. | 600/38 |
| 4,856,498 | * | 8/1989 | Osbon | 600/38 |
| 5,083,556 | * | 1/1992 | Osbon et al. | 600/39 |
| 5,094,230 | * | 3/1992 | Clark, Jr. | 600/38 |
| 5,195,943 | * | 3/1993 | Chaney | 600/38 |
| 5,421,808 | * | 6/1995 | Osbon et al. | 600/38 |
| 5,951,460 | * | 9/1999 | Vollrath | 600/38 |

* cited by examiner

*Primary Examiner*—Max Hindenburg
*Assistant Examiner*—Brian Szmal
(74) *Attorney, Agent, or Firm*—Hopgood, Calimafde, Kalil & Judlowe

(57) ABSTRACT

A technique for overcoming male impotence when this condition is due to a loss of plasticity in the tissues of the male organ, making it incapable of achieving and maintaining an erectile state. To practice this technique, the male organ to be treated is engaged by an erectile enhancement device which in the course of each operating cycle compels the organ to change from a flaccid to an erectile state and then revert to the flaccid state. The device is programmed to repeat this operating cycle a predetermined number of times during an exercise session that subjects the male organ to a workout that enhances the plasticity of the tissues. Impotence is overcome when the individual completes a series of such exercise sessions.

12 Claims, 1 Drawing Sheet

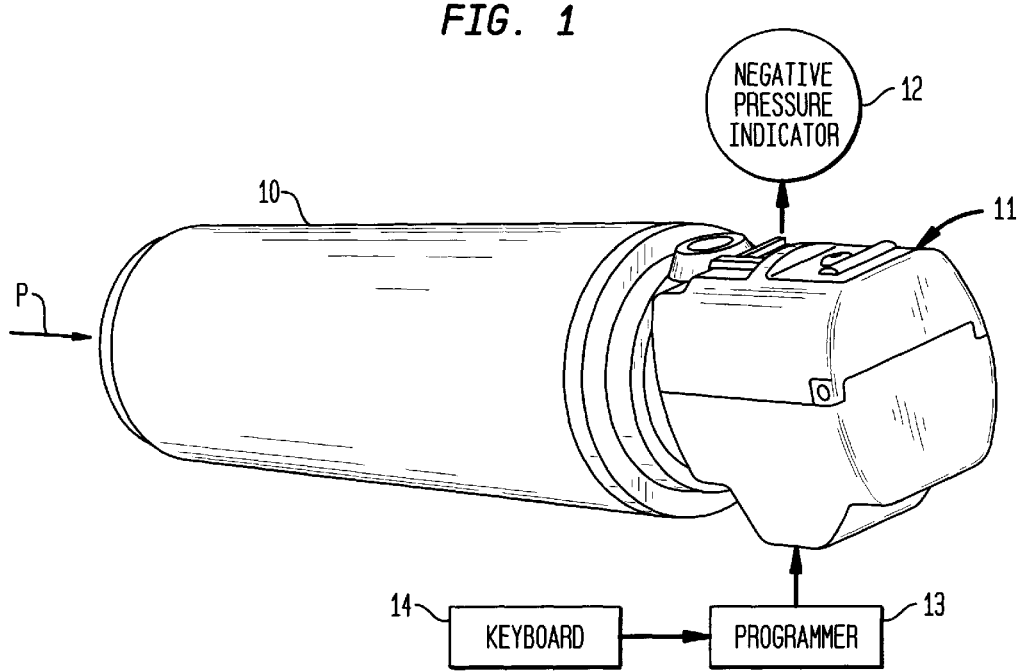
FIG. 1
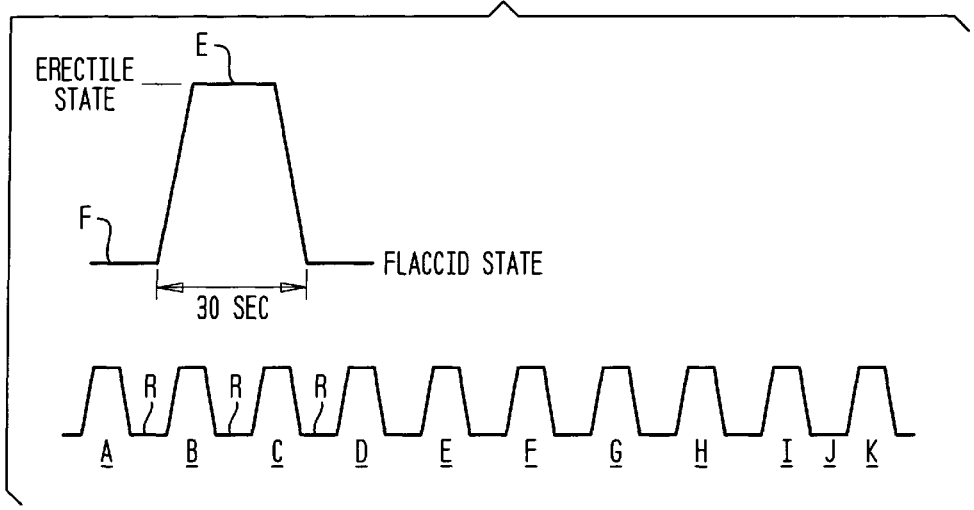
FIG. 2
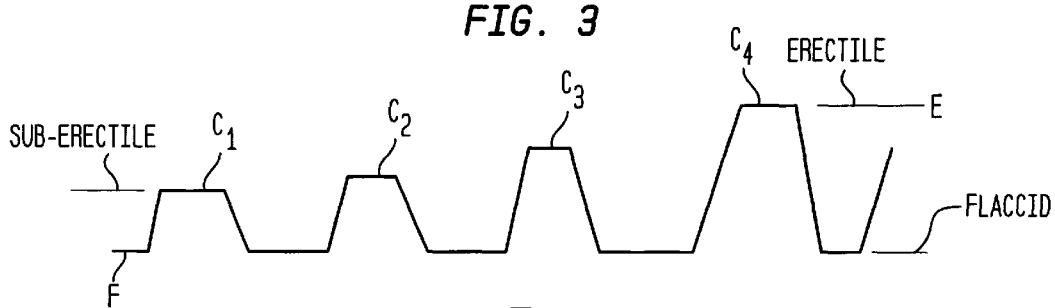
FIG. 3
FIG. 4

TECHNIQUE FOR RESTORING PLASTICITY TO TISSUES OF A MALE OR FEMALE ORGAN

BACKGROUND OF INVENTION

1. Field of Invention

This invention relates generally to the treatment of male impotence, and more particularly, to a technique for this purpose which is applied to a male organ whose tissues lack sufficient plasticity to achieve and maintain an erection, the technique acting to restore the plasticity of these tissues and thereby overcome impotence.

2. Status of Prior Art

Male impotence is an abnormal condition in which an individual is unable to achieve and maintain an adequate penile erection for coitus. Because male impotence is now widespread, it has attracted considerable medical and scientific interest directed toward finding an effective treatment therefor.

While male impotence is usually imputed to the aging process, it is by no means a condition confined to older men. Thus it is not unusual to find an individual of no more than 20 years of age exhibiting the early symptoms of male impotence.

Male impotence has often been attributed to psychological factors, such as stress, depression, financial worries and a failing marriage. But in our clinical experience with patients who suffer from male impotence, psychological factors account for only a small percentage of male impotence cases.

Various diseases, such as diabetes and multiple sclerosis may give rise to male impotence, and male impotence can also be an adverse side effect of some prescription drugs or result from substance abuse. However, in our clinical studies, these do not account for a high percentage of male impotence cases.

In these studies we have found that the most significant factor accounting for male impotence is the impaired physical fitness of the male organ, per se, separate and apart from all other considerations. Thus a subject who is free of disease and of psychological disorders, and who seemingly is in superb physical condition, may nevertheless be unable to perform sexually.

We have found that the physical fitness of a male organ depends on the plasticity of its tissues. Our studies show that the central core lesion in male impotence is a loss of plasticity so that the tissues of the organ are unable to stretch and expand to permit the organ to change from an initially flaccid state to an erectile state. It is only when the tissues of the male organ possess a normal degree of plasticity that the organ is then capable of achieving and maintaining the erectile state necessary for coitus and ejaculation. A loss of plasticity of the penile tissues of the corpus cavernosum renders the male organ incapable of expanding and contracting.

The loss of plasticity is not an overnight phenomenon, but is a gradual process which is insidious. As an individual experiences a gradual loss of plasticity, he then tend to reduce his sexual activity, for he finds it increasingly difficult to attain an erection. The resultant inactivity of the male organ gives rise to a further loss of plasticity until a point is reached where the individual becomes effectively impotent and is unable to function sexually despite the fact that he is otherwise healthy and in good physical condition.

The degree to which the tissues of a male organ possess or lack plasticity is easily determined. With normal plasticity, the organ feels rubbery and elastic, whereas when the organ loses plasticity, it becomes softer and mushy, sponge-like or flabby.

The male organ is composed of three columns of erectile tissue, two dorsolateral (corpa cavernosa) and one medial (corpus spongiosum) which contain the urethra and expands at the end to form the glans penis. The tissues support blood vessels that perform complex hemodynamic processes. For an erection to occur and be maintained, the arterioles, the veins as well as valves in the veins, must work in conjunction with changes taking place in the penile tissues. A loss of plasticity adversely affects the dynamics of flow in the arterioles and veins and impairs the ability of the valves in the venous system to operate properly.

During erection, the caverns of the corpus cavernosum fill with blood and dilate. This action stretches the smooth muscles lining the walls of these caverns and the connective tissue disposed therebetween. The two erectile cylinders then increase dramatically in size. When the erection thereafter subsides, the elastic recoil of the walls return the caverns to their normal size.

The ability of a male organ to achieve and maintain an erectile state therefore depends on the plasticity of its tissues, this plasticity determining the fitness of the sexual organ for its intended purpose.

As the ability to maintain an erection diminishes, there is a corresponding decline in the plasticity of the tissues. Both processes feed on each other in a spiraling descent leading to a condition of total impotence.

When male impotence is due to the loss of plasticity of the tissues of the penis, this condition cannot be overcome by the use of vasodilators, such as prostaglandins (Alprostadil). These drugs act to dilate the cavernosal arteries, resulting in an increased arterial inflow velocity. But should the tissues of the penis lack plasticity, the penis may not achieve and maintain an erectile state.

Heretofore, the treatment of male impotence was not calculated to overcome impotence, but to simulate potency by artificial means causing an impotent male organ to assume an erectile state.

To this end, the Lederer U.S. Pat. No. 1,225,341 places an impotent male organ in a vacuum chamber which acts to draw blood into the penis to induce vacuum engorgement. When the penis is in an engorged state it is then erect, this erection being secured by means of an elastic cincture band which acts as a tourniquet to prevent the blood from leaving the penis.

The Osborne U.S. Pat. Nos. 4,378,008, 5,083,556 and 4,856,498 disclose various types of vacuum enhancement devices in which a vacuum chamber is provided with a port into which a flaccid penis is inserted, the vacuum chamber being coupled to a manual pump.

Of greater prior art interest is the Osborne et al. U.S. Pat. No. 5,421,808. This patent discloses a self-contained battery-operated external vacuum device that includes an electric motor coupled to a reciprocating diaphragm pump. Because this vacuum device is electrically-powered, it is more easily regulated and controlled.

A vacuum erection device (VED), whether manually or electrically operated, does not cure impotence, but simply acts to simulate potency. Thus when this device by means of a negative pressure draws blood into the penis so that it is engorged, this imitates a normal erection. However to maintain this synthetic erection, the penis must be girded to prevent the blood from escaping.

While an individual who simulates an erection by means of a vacuum erection device can perform coitus, the engorged penis is effectively a dildo which is a poor substitute for a normally erect penis capable of ejaculating. Hence sexual activity made possible by a vacuum erection device in many respects falls short of natural coitus.

SUMMARY OF INVENTION

In view of the foregoing, the main object of this invention is to provide a technique for overcoming male impotence when due to a loss of plasticity of the tissues of the male organ, the technique acting to restore plasticity to the tissues.

More particularly, an object of the invention is to provide an electrically-powered apparatus of the above type in which a vacuum device acts to create a negative pressure that draws blood into the male organ engaged by the device, which device in the course of each operating cycle compels the organ to change from a flaccid to an erectile state and then revert to a flaccid state.

Yet another object of the invention is to provide a technique to overcome male impotence which when properly practiced has no adverse side effects.

Briefly stated, these objects are attained by a technique for overcoming male impotence when this condition is due to an insufficient plasticity of the tissues of the male organ to achieve and maintain an erectile state. To practice this technique, the male organ to be treated is engaged by an erectile enhancement device which in the course of each operating cycle for a predetermined number of times compels the organ to change from a flaccid to an erectile state and then revert to the flaccid state.

The device is programmed to repeat this operating cycle during an exercise session that subjects the male organ to a workout that enhances the plasticity of the tissues. Impotence is overcome when the individual completes a series of such exercise sessions.

BRIEF DESCRIPTION OF DRAWINGS

For a better understanding of the invention, as well as further features thereof, reference is made to the detailed description thereof to be read in connection with the annexed drawings wherein:

FIG. 1 is a block diagram of an apparatus for carrying out a technique in accordance with the invention to overcome male impotence;

FIG. 2 graphically illustrates one operating cycle of the apparatus;

FIG. 3 shows the operating pattern of an exercise session for effecting a workout of the tissues of the male organ being treated; and FIG. 4 shows another pattern of operating cycles.

DESCRIPTION OF INVENTION

A technique in accordance with the invention is applicable to a male organ that is more or less impotent because the tissues thereof have lost much of their normal plasticity or tone whereby the organ is then unable to achieve and maintain the erectile state necessary for coitus.

Inasmuch as a technique in accordance with the invention acts to exercise the tissues of a male organ as if it were a muscle, the term "tone" is appropriate to describe the condition of the tissues. In physiology, tone refers to the normal state of elastic tension or partial contraction in resting muscles. The term tone is more generally defined in Webster's Third New International Dictionary as "healthy or normal elasticity."

When muscles are flabby and lacking in tone, they are then incapable of carrying out strenuous muscular activity. One can restore the tone of muscles by exercise. Thus a typical exerciser for the arm muscles in a helical spring with a handle attached at either end. The user pulls these handles apart to stretch the spring and then permits the spring to contract during each operating cycle of this exerciser, thereby strengthening the arm muscles. But one cannot exercise the tissues of a male organ in the manner in which one exercises arm muscles.

In an apparatus for carrying out a technique in accordance with the invention as shown in FIG. 1, a vacuum erection device is provided, the device being composed of a vacuum chamber 10 and a self-contained, battery-operated pump assembly 11 coupled to one end of the chamber. Chamber 10 is preferably a cylinder of transparent plastic material, such as a polyacrylic, so that one can observe the male organ P received in the vacuum chamber.

In practice, the vacuum chamber and pump assembly may be of the type disclosed in the Osborne et al. U.S. Pat. No. 5,421,808 in which the vacuum chamber is tapered toward the penis-introducing end to facilitate full engorgement of the glans penis.

Coupled to assembly 11 is a negative pressure indicator 12 to permit a user to monitor the degree of negative pressure applied to penis P. And associated with assembly 11 is an electrical programmer 13 which is arranged to establish the timing of an operating cycle and of an exercise session appropriate to the individual being treated.

Exercise of the tissues of the organ is effected by a timed program in which during each operating cycle of the apparatus, as shown in FIG. 2, a male organ, initially in a flaccid state F at the start of the cycle, is subjected in the vacuum chamber to a negative pressure which draws blood into the organ and engorges the organ so that it assumes an erectile state E. In the course of an operating cycle, the vacuum is held to maintain the organ in an erectile state E for a brief interval, such as thirty seconds to a minute, after which the vacuum is released to cause the penis to revert to its flaccid state F.

This operating cycle acts to replicate the dynamics of achieving and losing an erection in the course of which the volume of the corpus cavernos is expanded and then contracted to simulate the natural process. The tissues of the male organ in the course of this operating cycle are stretched to attain the erectile state and then contract to re-assume the flaccid state.

In order to give the impotent male organ an exercise workout, it is necessary to repeat the operating cycle so that in the course of an exercise session, the penis is subjected to a succession of ten or more operating cycles A to K, as shown in FIG. 3. Between successive operating cycles in which the organ goes from a flaccid to an erectile state and back, there is a relaxation interval R. The duration of interval R which may be several minutes, is adjusted by programmer 13 so as to be tailored to the existing condition of the subject being treated.

It must be borne in mind that no two subjects suffer from the same degree of male impotence. No two subjects possess tissues exhibiting the same ability to recover their plasticity. Hence with each subject, one must observe his penis and the level of negative pressure necessary to produce an erectile state, using no more pressure than is necessary for this purpose. And one must empirically determine the tolerance of the subject to repeated operating cycles. Thus the number of operating cycles which make up an exercise session and relaxation interval between these operating cycles must be adjusted to accommodate the subject being treated.

It is usually desirable that the subject only go through at least one exercise workout session a day, with no more than five workouts a week. As to the time it takes for a subject being exercised to regain the potency of his organ, this depends on his physical condition and the amount of exercise necessary to restore the tone of his tissues. Hence in some instances, there is a marked improvement in tone in a matter of weeks, while in other cases it may take several months.

The clinical pattern of recovery involves a gradual, but steady increase in erectile function. We have treated over 400 patients with this technique and none have failed to show a positive response. While the VED exercise technique acts to restore potency, once it is restored and the subject can function sexually this does preclude further treatment. As with athletes, the way to maintain muscle tone is to continue to exercise, just as a concert pianist must practice daily to maintain his digital dexterity. And while a recovered subject need not exercise his penile tissues five days a week, as he did when striving to recover his potency, he should continue to exercise at least once a week.

In the operating cycle shown in FIGS. 1 and 2, the negative pressure is such as to cause the male organ P to go from a flaccid to a fully erectile state and then back to a flaccid state; this being repeated with each new operating cycle. But it may be desirable to progressively increase the degree of exertion so as not to overtax the tissues being exercised. Thus, as shown in FIG. 3, the first operating cycle $C_1$ may be arranged to cause the male organ to change from a flaccid state and to a sub-erectile state. This being about one half the level of the normal erectile state; the second cycle $C_2$ raises the level somewhat higher, and the third cycle $C_3$ raises it still higher, but below the full erectile state which is not attained until cycle $C_4$.

This progressive pattern of operating cycles is then repeated in a subsequent series of cycles. Programmer 13 is provided with a keyboard 14 so that the operator of the apparatus can enter into the device timing parameters appropriate to the subject being treated.

While a technique in accordance with the invention serves to overcome male impotence, the said technique is useful in forestalling such impotence. Thus many men only occasionally experience difficulty in having an erection and are by no means impotent. Yet these men can benefit from the penile exercise technique, for an occasional penile exercise workout acts to maintain the fitness of the organ.

The technique is also beneficial in the treatment of female impotence when due to the loss of plasticity of the tissues of the clitoris whose tissues are similar to those of the male organ. But in order to exercise the tissues of the clitoris, the vacuum chamber for this purpose must be adapted to accommodate the clitoris such that when a negative pressure is produced, this draws blood into the clitoris which then becomes engorged.

While there has been disclosed a technique in accordance with the invention for restoring plasticity to tissues of a sexual organ, it will be appreciated that many changes may be made therein without departing from the spirit of the invention.

We claim:

1. A technique for overcoming impotence due to a loss of plasticity of the tissues forming the sexual organ; said technique comprising the steps of:

A. subjecting the organ to be treated to an operating cycle in the course of which the organ is changed from a flaccid to an erectile state and then back to a flaccid state to cause the tissues to expand and contract; and B. repeating the operating cycle a predetermined number of times to complete an exercise session that constitutes a workout of the organ and enhances the plasticity of the tissues.

2. A technique as set forth in claim 1, in which the sexual organ is a penis.

3. A technique as set forth in claim 1, in which the sexual organ is a clitoris.

4. A technique as set forth in claim 1, in which the operating cycle is produced by a vacuum erectile device having a vacuum chamber in which the organ is received, the vacuum during operating cycle producing a negative pressure causing blood to be drawn into the organ to render it erect.

5. A technique as set forth in claim 4, in which the vacuum erectile device includes a battery-operated pump associated with the vacuum chamber to expel air therefrom.

6. A technique as set forth in claim 5, in which the chamber is transparent so that the organ can be observed and its condition determined.

7. A technique as set forth in claim 5, in which the vacuum erectile device is programmed so that in the course of an exercise session, it undergoes a predetermined number of operating cycles.

8. A technique as set forth in claim 1, in which the exercise sessions are repeated over an extended period of time sufficient to cause the organ to go from a condition in which it is flabby to a condition in which it is rubbery.

9. A vacuum erectile device for treating a sexual organ that is impotent due to a loss of plasticity of the tissues forming the organ said device comprising:

A. a vacuum chamber in which the organ to be treated is received;

B. an electrically-powered vacuum pump coupled to the chamber for drawing air therefrom to produce a negative pressure drawing blood into the organ to cause it to assume an erectile state; and C. control means coupled to the electrically-powered vacuum pump to cause it to undergo an operating cycle in the course of which the organ is changed from a flaccid to an erectile state and then back to a flaccid state, causing the tissues to expand and contract.

10. A device as set forth in claim 9, in which said control means is programmed acts to repeat the operating cycle a predetermined number of times during an exercise session that constitutes an exercise workout of the organ that enhance the plasticity of the tissues.

11. A device as set forth in claim 9, further including an indicator coupled thereto to indicate the prevailing level of negative pressure in the chamber.

12. A device as set forth in claim 10, in which the chamber is formed of transparent synthetic plastic material.

* * * * *